Figure 1:
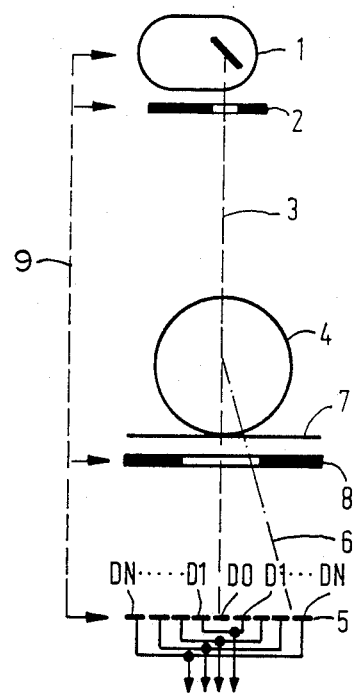

United States Patent [19]

Harding et al.

[11] Patent Number: 4,754,469

[45] Date of Patent: Jun. 28, 1988

[54] METHOD FOR THE DETERMINATION OF THE SPATIAL DISTRIBUTION OF THE SCATTERING CROSS-SECTIONS FOR ELASTICALLY SCATTERED X-RAY RADIATION AND ARRANGEMENT FOR IMPLEMENTATION OF THE METHOD

[75] Inventors: Geoffrey Harding, Halstenbek; Josef-Maria Kosanetzky, Norderstedt; Ulrich Neitzel, Hamburg, all of Fed. Rep. of Germany

[73] Assignee: U.S. Philips Corp., New York, N.Y.

[21] Appl. No.: 884,452

[22] Filed: Jul. 11, 1986

[30] Foreign Application Priority Data

Jul. 20, 1985 [DE] Fed. Rep. of Germany ....... 3526015

[51] Int. Cl.$^4$ .......................................... G01N 23/201
[52] U.S. Cl. ........................................ 378/88; 378/86
[58] Field of Search ............... 378/5, 6, 82, 83, 86–88, 378/90

[56] References Cited

U.S. PATENT DOCUMENTS

| 3,936,638 | 2/1976 | Gibbons | 378/6 |
| 4,028,554 | 6/1977 | Hounsfield | 378/5 |
| 4,121,098 | 10/1978 | Jagoutz et al. | 378/83 |
| 4,123,654 | 10/1978 | Reiss et al. | 378/90 |

FOREIGN PATENT DOCUMENTS 0153786 9/1985 European Pat. Off. ........ 378/7

Primary Examiner—Janice A. Howell
Assistant Examiner—John C. Freeman
Attorney, Agent, or Firm—Paul R. Miller

[57] ABSTRACT

The invention relates to a method for determination of the cross-sections for elastic scattered radiation in which a polychromatic radiation source is used but in which good differentiation between various substances is still possible.

3 Claims, 2 Drawing Sheets

METHOD FOR THE DETERMINATION OF THE SPATIAL DISTRIBUTION OF THE SCATTERING CROSS-SECTIONS FOR ELASTICALLY SCATTERED X-RAY RADIATION AND ARRANGEMENT FOR IMPLEMENTATION OF THE METHOD

The invention relates to a method for the determination of spatial distribution of the scattering cross-sections for elastically scattered x-ray radiation in an area of examination irradiated with a primary beam of small cross-section, wherein the scattered radiation leaving the area of examination at different angles is detected by a number of detectors and wherein the energy of the X-ray quanta in the primary beam and the angular range in which the detectors detect the scattered radiation are selected in such a way that the proportion of elastically scattered radiation is predominant. The invention also relates to an arrangement for implementing the method.

Such an arrangement is known from the article in Phys. Med. Biol., 1985, Vol. 30, No. 2, pages 183–186.

This method utilizes the fact that scattered radiation which forms only a small angle with the direction of the primary beam (e.g. smaller than 12°) consists mainly of elastically scattered radiation, if the energy of the X-ray quanta is not too high. In contrast to non-elastically scattered radiation (Compton scattered radiation) the energy spectrum of elastically scattered radiation corresponds to that of the primary beam of rays. The elastic scattered radiation has a marked angular dependence with a pronounced maximum which has a position depending on the irradiated material and the hardness of the radiation in the primary beam and lies between 1° and approx. 19°.

In the known method—in a manner similar to a first-generation computer tomograph—a relative displacement takes place between the primary beam and the area of examination at right angles to the primary beam until the entire area of examination has been irradiated, following which the direction is changed such that the X-ray radiator irradiates the area of examination, after which a lateral displacement takes place again, etc. At each of the angular and displacement positions of the primary beam with respect to the area of examination, the intensity of the radiation is detected at different scattering angles and usually also in the primary beam itself. If, each time, use is made only of the measured values which are assigned to a scattering angle, i.e. a particular detector, then it is possible to reconstruct for this scattering angle the spatial distribution of the scattering cross-sections for elastically scattered radiation. Distributions for other scattering angles can be similarly reconstructed from the measured values of the other detectors. Because of the strong dependence of the scattering intensity on the chemical composition of the scattering center causing the scattering process within the primary beam, these reconstructions of the distribution of the elastic scattering cross-sections, classified according to scattering angles, differ considerably so that, for example, different substances having the same absorption capacity (meaning that they cannot be differentiated in a normal computer tomogram) are able to be distinguished one from another in reconstructed scattering cross-section distributions which are classified by scattering angles, if these substances have different cross-sections for the scattering angles concerned.

For the radiation source it is possible to use a monochromatic radiation source, e.g. a radioisotope. Different substances can be very well distinguished from one another by this means, but these sources of radiation usually have such a low intensity that relatively long measuring times are required. If an X-ray tube having a much larger intensity is used instead, then the desired shorter measuring times are indeed obtained, but different materials can no longer also be differentiated from one another because the X-ray radiation is polychromatic and the dependence of the scattering cross-sections on the scattering angle is much less pronounced than in the case of monochromatic radiation.

It is the aim of the present invention therefore to develop a method of the type described in the preamble such that different substances can be satisfactorily distinguished from one another even when a polychromatic source of radiation, for example an X-ray tube, is used.

The invention achieves this aim as follows: the energy of the X-ray quanta is measured and the detected X-ray quanta are arranged in groups and counted, each group containing the X-ray quanta for which the product of scattering angle and energy is at least approximately equal.

At this point it should be mentioned that from German Offenlegungsschrift No. 24 32 305, corresponding to U.K. patent specification No. 1,463,054, and U.S. Pat. No. 3,936,638, a method is already known for the determination of scattering cross-sections in an area of examination wherein the area is irradiated with a primary beam of small cross-section and the radiation leaving the area of examination is separately detected with a number of detectors measuring the energy of the individual X-ray quanta. In this method, however, X-ray radiation of such hardness (between 200 keV and 2 MeV) is used that the radiation is considerably attenuated by Compton scattering. In the case of attenuation of the radiation by Compton scattering, the energy of the scattered X-ray quanta is known to decrease as a function of the particular scattering angles. In the known method the energy of the X-ray quanta is now measured in order to be able to determine from it this scattering angles and thus the location of the scattering center in the area of examination and inside the primary beam so that the scatter density distribution along the primary beam can be reconstructed in one position of the primary beam with respect to the area of examination.

The invention is based therefore on the fact that the scattering angle, at which the scattering cross-section has a maximum for a given substance, is dependent on the energy of the X-ray radiation, and to such an extent that this scattering angle is at least approximately inversely proportional to the energy of the X-ray quanta. If, therefore, the X-ray quanta are counted in groups, whereby each group includes the X-ray quanta with which the product of the measured energy and the scattering angle (which is given essentially by the arrangement of the particular detector with respect to the primary beam) attains a specific value at least approximately, then each group contains precisely those X-ray quanta which—in the case of monoenergetic radiation—would be assigned to a definite scattering angle. If, therefore, the reconstruction of the scatter density distribution is carried out separately according to these groups, then different substances can be distinguished equally as well as in the case of monochromatic X-ray radiation.

Figure 2:
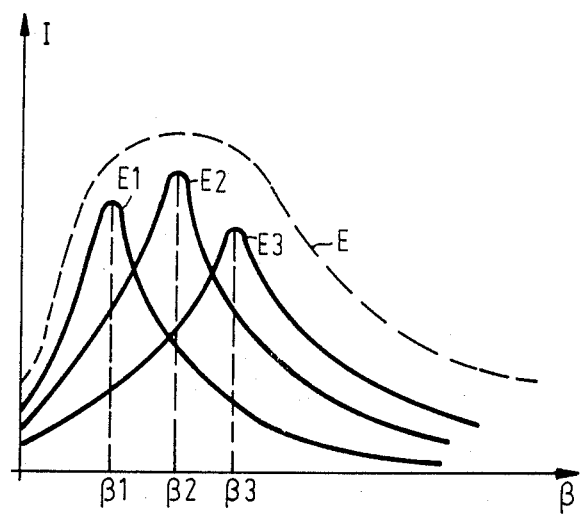
Figure 3:
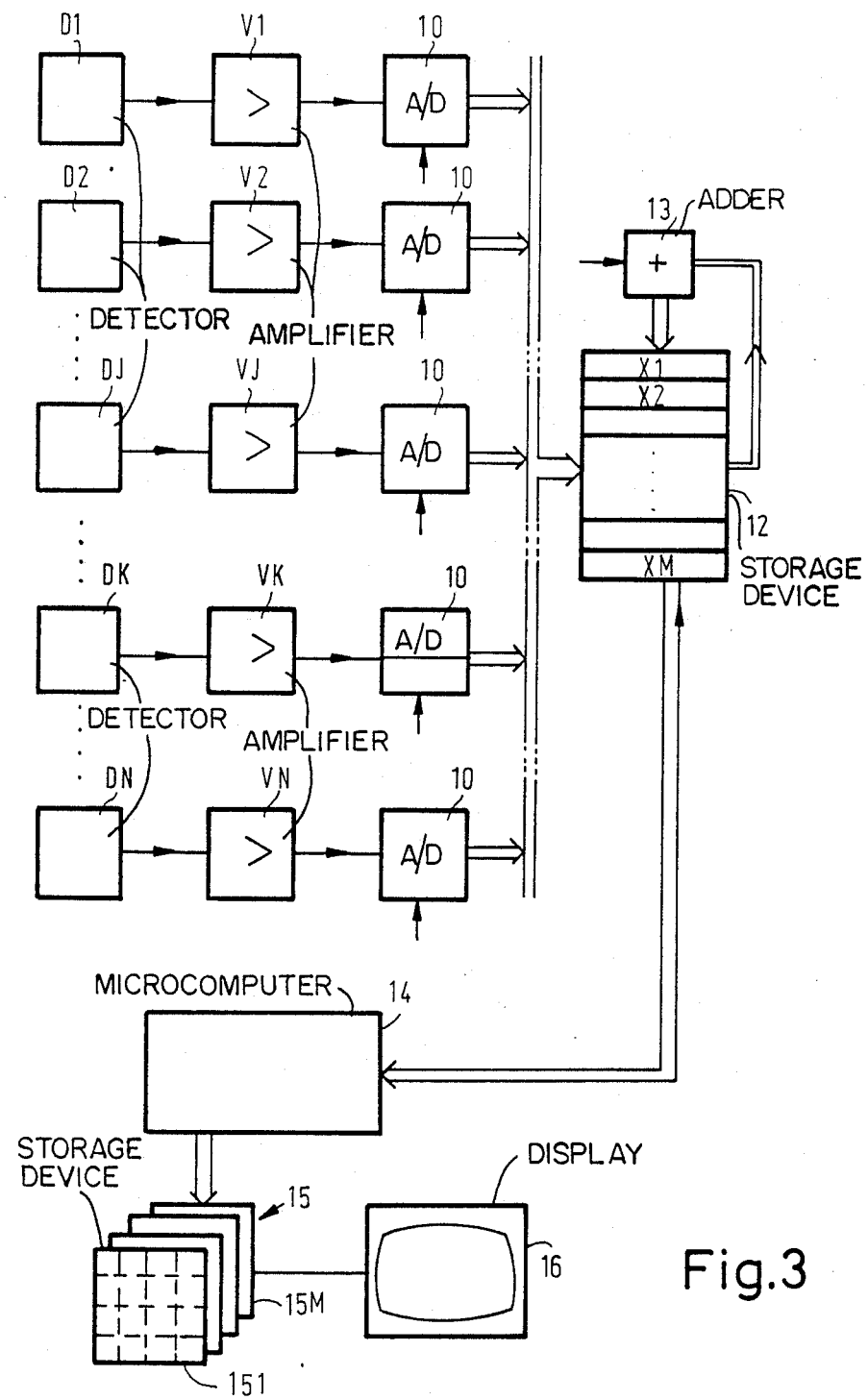

The invention will be explained in more detail below with the aid drawings which show:

FIG. 1 the mechanical arrangement for detection of the scattered radiation in schematic representation, FIG. 2 the dependence of the radiation intensity on the scattering angle in the case of a given substance for different energies of the X-ray quanta, and FIG. 3 a circuit for processing the signals supplied by the detectors.

In FIG. 1, 1 represents a radiation source in the form of an X-ray radiator 1 having in the radiation path a diaphragm 2 which masks a primary beam of small cross-section into its direction of propagation (pencil beam). The primary beam 3 passes through an area of examination 4 in which a body, but also a technical object, can be arranged. On the other side of the examination area 4—with respect to the radiation source— there is a detector arrangement 5 comprising a number of detectors D0, D1 ... DN. Detector D0 is arranged in the primary beam, while the other detectors D1 ... DN are on arcs arranged concentrically to this and are preferably annular in shape. Detectors D0, D1 ... DN are configured in such a way that the amplitude of the electrical pulses, which are generated during the detection of an X-ray quantum, is proportional to the energy of the X-ray quantum concerned. These detectors may, for instance, be semiconductor detectors, e.g. germanium detectors or scintillation detectors, or possibly thallium-activated sodium iodide detectors. For the sake of simplicity, only five detectors are shown in the drawing (N=4). In practice, however, substantially more detectors should be used, e.g. N=30.

Detectors D1 ... DN detect, each time, the scattered radiation which is generated in the primary beam 3 and in the examination area 4 and which leaves at a given angle with respect to the primary beam or in a small area about this angle. A definite angle therefore is allocated to each detector. If this allocation should prove too inaccurate, then it can be corrected as described in the older German patent application No. P 34 06 905, which correpsonds to European patent No. 153786, in conjunction with FIGS. 2 and 3. The angle at which the detectors detect the scattered radiation is restricted to approx. 10°; and the angle at which the scattered radiation 6 from the area of examination impinges on the most extreme detector DN is therefore approx. 10°. In the case of larger angles the proportion of the elastic scattered radiation is too small with the tube voltages used (smaller than 150 kV).

Between the body 4, which is positioned on the tabletop 7 of an examination table not illustrated in detail, and the detector arrangement 5 there is a further diaphragm 8 having an aperture dimensioned such that the scattered radiation generated in the primary beam inside the examination area 4 can just impinge on detector DN. By this means it is possible to suppress the influence of the multiply scattered radiation in the examination area 4. This multiply scattered radiation can be suppressed even better if lamellae of radiation-absorbing material, not illustrated in detail, are arranged in the form of a truncated cone between the detector arrangement 5 and below the examination area 4 in such a way that each detector can detect through these lamellae only the part of the examination area which is permeated by the primary radiation.

As indicated by the dashed line 9, the radiation source 1, the diaphragms 2 and 8 and the detector arrangement 5 are mechanically coupled to one another so that a relative movement between this arrangement and the examination area 4 is possible. For the detection of a plane examination area—as in the case of the first generation computer tomographs—the primary beam 3 is displaced laterally so that it successively passes through the plane examination area and the body is then turned, following which the primary beam is displaced in the same plane etc until each detector has detected the scattered radiation in a plurality of angular positions and displacement positions. To the extent described so far, the arrangement is largely known from the above-described article in Phys. Med. Biol., 1985, Vol. 30, No. 2, pages 183–186 and is described in the above-mentioned older patent application No. P 34 06 905.

FIG. 2 shows the pattern of the scattering intensity for one substance as a function of the scattering angle for different energies E1, E2, E3, which are related to one another as follows: E1>E2>E3. It can be seen that the intensity. i.e. the number of recorded X-ray quanta per unit time has a pronounced maximum for each energy. A substance with a different chemical composition has a different curve form for the same energy, but also with a pronounced maximum. Because of this pronounced angular dependence it is possible, therefore, to clearly distinguish between the two substances if X-ray radiation with only one energy (e.g. only E3) is used, i.e. monochromatic X-ray radiation. However, the intensity of monochromatic X-ray sources, e.g. radioisotopes, is very low which would mean long measuring times. An X-ray tube supplies X-ray radiation of much higher intensity which means that shorter measuring times result. However, X-ray tubes have a continuous (bremsstrahlung) spectrum with a maximum energy in key corresponding to the voltage at the X-ray tube (in kV). Because all the energies are represented in this spectrum right up to this limiting energy, it becomes clear that in the case of such an energy spectrum the intensity plotted against the scattering angle has only a slightly pronounced, broad maximum, as indicated by the dashed line E in FIG. 2. The corresponding curve for another substance is, in fact, not fully identical with this, but has a very broad area of overlap which means that it is difficult to distinguish two different substances from one another on the basis of the scattering angle dependence of the intensity of the elastically scattered radiation.

The invention utilizes the fact that there is a relationship $$E1^*\sin(\beta\tfrac{1}{2}) = E2^*\sin(\beta 2/2) = X$$

between the energy of the X-ray quanta and the scattering angle. In this equation, $\beta 1$, $\beta 2$, $\beta 3$ are the scattering angles for the energies E1, E2 and E3 respectively. In the case of small angles, however, $\sin(\beta) = \beta$ can be used without great error so that $$E1^*\beta 1 = E2^*\beta 2 \mu X$$

The product of energy and scattering angle is proportional to the so-called momentum transfer X. The curve form of the intensity of the X-ray radiation, i.e. the number of X-ray quanta per unit time, as a function of this product in the case of polychromatic radiation, is approximately the same shape as the curve of the intensity of the radiation plotted against the scattering angle in the case of monochomatic radiation. If, therefore, the product of the energy of the quantum and the scattering angle is determined for each X-ray quantum and a count is taken of the X-ray quanta which in each case exhibit the same product, then it is possible to clearly distinguish between two different substances on the basis of the different curves of the number of X-ray quanta as a function of the product.

FIG. 3 shows a circuit which appropriately processes the signals of detectors D1 ... DN. In this circuit, each detector is allocated a channel which, in addition to the detector itself, comprises a subsequent amplifier V1, V2 ... VN and a high-speed analog-digital converter 10 which converts the output signal of the preceding amplifier into a binary-coded digital data word.

The gains of amplifiers V1 ... VN are proportional to the scattering angles $\beta 1 \ldots \beta N$ at which the subsequent detectors detect the scattering radiation in each case. If, therefore, detector DJ, for instance, detects the scattered radiation at an angle $\beta$ and detector DK detects it at an angle $n\beta$, where n is a factor greater than 1, then the gain of the amplifier VK connected after detector DK is greater by the factor n than the gain of amplifier VJ. For this reason and because the amplitude of the output signals of the detectors is proportional to the energy of the detected X-ray quantum, signals having an amplitude, proportional to the product of the scattering angle and the energy of the X-ray quantum appear at the output of amplifiers V1 ... VN during the detection of X-ray quanta by the corresPonding detector D1 ... DN.

The digital-analog converters must be of a sufficiently high speed to be able to generate a signal, representing the amplitude of the output signal of amplifier V1, during each detection of an X-ray quantum by the preceding detector. They can each, for example, contain a capacitor which is charged via a peak-value rectifier by the output pulse of the preceding amplifier and which is subsequently fully discharged again by a constant current. The discharge time in this case is proportional to the product of the energy of the X-ray quantum and the gain of the preceding amplifier, i.e. to the scattering angle of the preceding detector. The discharge time is measured by means of an electronic counter register which during the discharge period counts the pulses of a constant-frequency oscillator, the start of the capacitor discharge being synchronized with the oscillator pulses. The trigger signals for the analog-digital converter 10 are derived for this from the output signals of the preceding detectors.

The outputs of the digital-analog converters 10 are coupled to the address inputs of a storage device 12. Each time one of the converters has converted a voltage pulse into a digital data word, the address corresponding to this data word in storage device 12 is called up. At the same time an adder 13 is activated which adds a 1 to the content of the storage location called up and writes the result to the same storage device. Therefore, in a defined position of the primary beam with respect to examination area, i.e. during a measurement, a count is taken at the different storage locations of storage device 12 of those X-ray quanta whose product X1, X2 ... XM of quantum energy and scattering angle has approximately the same value in each case. Thus the converters 10, in conjunction with the storage device 12 and the adder 13, act as pulse height analyzers.

The number of groups X1 ... XM, to which the X-ray quanta are assigned, should be approximately twice as large as the number of detectors. Because the storage device 12 and the adder 13 have to process signals from all N channels, they must have a high processing speed at high counting rates. For the situation where the processing speed is inadequate, a storage device 12 and an adder 13 can be provided for each channel or for some of the channels in each case. At the end of the measurement, only the storage contents corresponding to the same product X1, X2 or XM need to be added.

After each measurement the values stored in storage device 12 are called up and further processed in a microcomputer 14 as described, for example, in the previously mentioned German patent application No. P 34 06 905. For each measurement a correction can be made here according to the attenuation of the primary radiation by the body. This attenuation is obtained from the output signal of the detector DO which is arranged in the primary beam. If all the measurements are carried out in this way, the microcomputer can separately calculate for each product X1, X2 ... XM the scatter distribution at the individual points of the examination plane and store these values in a storage device 15 which has a separate memory area 151 ... 15M for each product X1 ... XM. In order to prevent the properties of the system (e.g. the radiation spectrum of the X-ray tube, the detector characteristic etc.) from influencing the reconstruction of the distribution of the scattering cross-sections, it is necessary to divide the values obtained for the different products X1, X2 ... XM by reference values which are obtained for the same products from calibration measurements on a calibration body of, preferably, Plexiglas. The standardized values thus obtained represent therefore the relative scattering function with respect to the reference medium. This calibration measurement need be carried out only once if the measuring conditions do not change with time. When conditions are not constant it must be repeated, e.g. every time before and/after an examination.

The images obtained in this way can be fed to a display unit 16—separated once again according to products X1 ... XM. The pictures thus obtained show therefore for each picture point the pattern of the scattering intensity as a function of X or as a function of the scattering angle. This provides information about the chemical composition of the irradiated area.

Instead of using an amplifier with appropriately adjusted gain, the product of energy and scattering angle in the individual channels could also be obtained by means of a multiplier stage connected after the converters 10 or by designing the converters as multiplying digital-analog converters; however, the cost of this would normally be greater than that of the solution depicted in FIG. 3.

What is claimed is:

1. Method for determining the spatial distribution of the scattering cross-sections for elastically scattered X-ray radiation passing through an area of examination comprising the steps of: irradiating, with a primary X-ray beam of small cross-section, the area of examination; detecting the scattered radiation leaving the examination area at different angles using a plurality of detectors; selecting the energy of the X-ray quata in the primary beam and the angular range at which the detectors detect the scattered radiation so that the proportion of elastically scattered radiation predominates therein; measuring the energy of the X-ray quanta; determining the spatial distribution of the scattering cross-section for elastically scattered X-ray radiation by ordering the detected X-ray quanta into groups; and counting the number of detected quanta in each group where each group comprises the X-ray quanta for which the product of scattering angle and energy is at least approximately the same.

2. Arrangement for implementing spatial distribution of scattering cross-sections for elastically scattered X-ray radiation comprising an X-ray radiator providing a primary beam of X-rays;

means for masking said primary beam to form rays of small cross-section;

detectors with defined spatial positions relative to said primary beam; and means for displacing said rays of small cross-seciton at an area of examination, wherein the improvement comprises said detectors being configured during detection of X-ray quanta to generate pulses having an amplitude dependent on energy of the X-ray quanta;

pulse height discriminators connected after said detectors;

means for generating signals proportional to the product of measured energy and scattering angle; and storage means for storing the number of times said product signals achieve a given value corresponding to a given area of examination.

3. Arrangement according to claim 2, wherein amplifier means are connected between each detector and a corresponding pulse height discriminator, wherein said amplifier means has a gain proportional to said scattering angle, and wherein each said detector coupled to said amplifier means detects scattered radiation for said scattering angle.

* * * * *